(12) United States Patent
Nanjo et al.

(10) Patent No.: US 7,052,134 B2
(45) Date of Patent: May 30, 2006

(54) FUNDUS CAMERA

(75) Inventors: Tsuguo Nanjo, Toyohashi (JP);
Naohisa Shibata, Gamagori (JP)

(73) Assignee: Nidek Co., Ltd. (JP)

( * ) Notice: Subject to any disclaimer, the term of this patent is extended or adjusted under 35 U.S.C. 154(b) by 532 days.

(21) Appl. No.: 10/446,654

(22) Filed: May 29, 2003

(65) Prior Publication Data

US 2004/0252276 A1    Dec. 16, 2004

(51) Int. Cl.
*A61B 3/14* (2006.01)

(52) U.S. Cl. .................................. 351/206; 396/18
(58) Field of Classification Search ................ 351/206; 382/128; 396/18
See application file for complete search history.

(56) References Cited

U.S. PATENT DOCUMENTS

| 5,446,509 A | * | 8/1995 | Okinishi | .................... | 351/206 |
| 5,543,865 A | * | 8/1996 | Nanjo | ........................ | 351/206 |
| 6,325,511 B1 | * | 12/2001 | Mizuochi | .................... | 351/206 |
| 2001/0024263 A1 | | 9/2001 | Nanjyo | | |

FOREIGN PATENT DOCUMENTS

JP    11-332832    12/1999
JP    2001-258847    9/2001

OTHER PUBLICATIONS

High Performance Digital Imaging System VK-2 User's Guide. Version 1.22. Kowa Company Ltd., Publication date Mar. 15, 2002.*

* cited by examiner

*Primary Examiner*—Eric F. Winakur
*Assistant Examiner*—Theodore Shih
(74) *Attorney, Agent, or Firm*—Rader, Fishman & Grauer PLLC

(57) ABSTRACT

A fundus camera capable of obtaining a fundus image while keeping a fixed field angle even if an eye is not emmetropia, and advantageously utilizing a photographed image for diagnosis. The camera includes a photographing optical system having a photographing optical axis, a focusing lens arranged movable along the axis in an optical-axis direction, and a first element which picks up a fundus image illuminated with illumination light for photographing via the lens, a unit which moves the lens, a unit which detects a position of the lens, a display, and a display control unit which synthesizes the fundus image picked up by the element within an opening of a display frame figure, a size of the opening determined by a detection result of the detecting unit, to display as an image keeping a fixed field angle regardless of visibility of the eye, and displays on the display.

8 Claims, 4 Drawing Sheets

FUNDUS CAMERA

BACKGROUND OF THE INVENTION

1. Field of the Invention

The present invention relates to a fundus camera for photographing a fundus of an eye to be examined.

2. Description of Related Art

For a fundus camera, a 35-mm film is historically used as a basic image pickup medium, and a display frame (a mask or a field diaphragm) is fixedly arranged to limit a photographing range to a surface of the film which is an image forming surface. Also, for a recent fundus camera capable of electronic photography (image-pickup), a display frame is used, which is similar to that arranged when the 35-mm film is used.

Besides, in the fundus camera, focus adjustment to a fundus surface is performed by moving a focusing lens in order to correct a refractive error of an eye to be examined. However, when the focusing lens is moved, a photographing magnification is changed, and an image circle of a fundus image expands outside the display frame or shrinks inside it.

FIGS. 4A to 4C are views showing a state of the fundus image obtained when the focusing lens is moved in order to correct the refractive error. Reference numeral 100 is an objective lens, 101 is a focusing lens which moves along a photographing optical axis in an optical-axis direction, 102 is an image forming lens, 103 is a display frame being fixedly arranged, 104 is a relay lens, and 105 is a CCD camera which is an image pickup medium. If the fundus image when the focus adjustment is made with the eye to be examined under the conditions of emmetropia (0D(diopter)) as shown in FIG. 4A is taken as a reference, the fundus image when the focus adjustment is made with the eye to be examined under the conditions of myopia (−D) as shown in FIG. 4B forms such a shape where an image circle 106 thereof is expanded outside an display frame image 103a. On the other hand, the fundus image when the focus adjustment is made with the eye to be examined under the conditions of hypermetropia (+D) as shown in FIG. 4C forms such a shape where an image circle 107 thereof is shrunk inside the display frame image 103a (the blurred image circle 107 appears). Incidentally, S is a position of the lens 101 when the focus adjustment is made with the eye to be examined under the conditions of emmetropia (a standard position).

As mentioned above, the display frame fixedly arranged determines an actual photographing range of the fundus, however, the display frame may exactly be in consistent with a field angle only in the case where the eye to be examined is under the conditions of emmetropia. To cope with this problem, there is no other solution but to take a measure such that the blurred image circle does not appear even if the eye to be examined is not under the conditions of severe hypermetropia (+D), by setting the display frame as small as possible within the range of a predetermined standard (field angle) or other methods.

SUMMARY OF THE INVENTION

The present invention has been made in view of the above circumstances and has an object to overcome the above problems and to provide a fundus camera capable of obtaining a fundus image while keeping a fixed field angle even if an eye to be examined is not under the conditions of emmetropia, and capable of advantageously utilizing a photographed image for diagnosis.

To achieve the objects and In accordance with the purpose of the present invention, a fundus camera is provided with a photographing optical system having a photographing optical axis, a focusing lens arranged movable along the photographing optical axis in an optical-axis direction, and a first image pickup element which picks up an image of the fundus illuminated with illumination light for photographing via the focusing lens, a moving unit which moves the focusing lens, a detecting unit which detects a position of the focusing lens, a display, and a display control unit which synthesizes the fundus image picked up by the first image pickup element within an opening of a display frame figure, a size of the opening being determined based on a result of detection obtained by the detecting unit, to display as an image keeping a fixed field angle regardless of visibility of the eye, and displays the fundus image on the display.

In another aspect of the present invention, a fundus camera is provided with a photographing optical system having a photographing optical axis, a focusing lens arranged movable along the photographing optical axis in an optical-axis direction, and a first image pickup element which picks up an image of the fundus illuminated with illumination light for photographing via the focusing lens, a moving unit which moves the focusing lens, a detecting unit which detects a position of the focusing lens, a display, and a display control unit which trims the fundus image picked up by the first image pickup element into a size based on a result of detection obtained by the detecting unit, to display as an image keeping a fixed field angle regardless of visibility of the eye, and displays the fundus image on the display.

Additional objects and advantages of the invention are set forth in the description which follows, are obvious from the description, or may be learned by practicing the invention. The objects and advantages of the invention may be realized and attained by the fundus camera in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
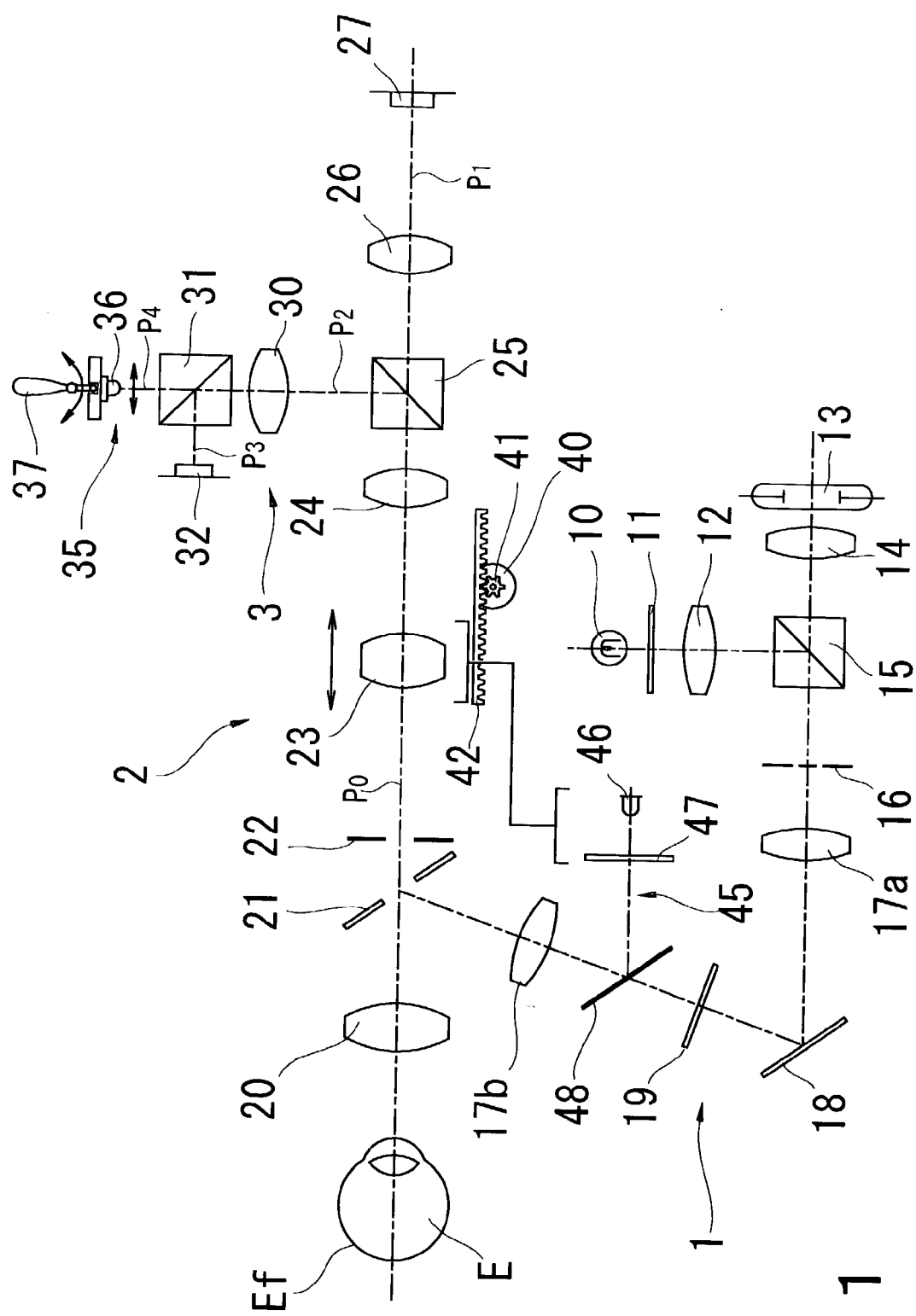
FIG. 1 is a view showing a schematic configuration of an optical system of a fundus camera consistent with an embodiment of the present invention.

A detailed description of one preferred embodiment of a fundus camera embodying the present invention will now be given referring to the accompanying drawings. FIG. 1 is a view showing a schematic configuration of an optical system of the fundus camera of non-mydriasis type consistent with a preferred embodiment of the present invention. The optical system includes an illumination optical system 1, a photographing optical system 2, an observation optical system 3, a fixation target projection optical system 35, and a focus index projection optical system 45.

Illumination Optical System

Illumination light emitted from a halogen lamp 10, which is an illumination light source for observation, is changed into infrared illumination light by using an infrared filter 11 having a property of transmitting only infrared light. After passing through a condenser lens 12, the infrared illumination light is reflected by a dichroic mirror 15 having a property of reflecting infrared light and transmitting visible light, and it illuminates a ring slit 16 having a ring-shaped aperture. Instead of the halogen lamp 10, other kinds of infrared light sources, such as an infrared LED and the like, may be used, and the filter 11 is not required in this case. Further, after visible illumination light emitted from a flash lamp 13, which is an illumination light source for photographing, passes through a condenser lens 14, it is transmitted through the dichroic mirror 15 so that an optical axis thereof is coaxial with an optical axis of the infrared illumination light to illuminate the ring slit 16. Besides, instead of the dichroic mirror 15, a half mirror may be used.

After passing through the slit 16, the illumination light (ring slit light) forms an intermediate image near an aperture in an apertured mirror 21 via a relay lens 17a, a mirror 18, a black dot plate 19 having a small black dot on its center, a half mirror 48, and a relay lens 17b, whereby the light is reflected so that an optical axis thereof is coaxial with an optical axis of the photographing optical system 2. After the illumination light (ring slit light) reflected by the mirror 21 once converges through an objective lens 20 near a pupil of an eye E to be examined, it diffuses to evenly illuminate a fundus Ef of the eye E. When the illumination light (ring slit light) enters the objective lens 20, a little light is reflected and becomes detrimental light to observing and photographing an image of the fundus Ef, but the detrimental light is absorbed by the small black dot placed in the center of the black dot plate 19.

Photographing Optical System

Reflected light from the fundus Ef passes through the lens 20, the aperture in the mirror 21, a photographic diaphragm 22, a focusing lens 23 which is movable along the photographing optical axis in an optical-axis direction, and an image forming lens 24, and then it enters a dichroic mirror (dichroic prism) 25 having a property of reflecting infrared light, transmitting about 80% to 90% of visible light and reflecting the residual visible light accounting for about 20% to 10%. visible reflection light from the fundus Ef, having passed through the dichroic mirror 25, via a relay lens 26, which relays light from the lens 24 in accordance with its purpose, enters a color CCD camera 27 for photographing having a sensitivity to the visible range, and forms the image of the fundus Ef on an image pickup surface of the camera 27.

Observation Optical System

The observation optical system 3 shares the elements from the lens 20 to the dichroic mirror 25 with the photographing optical system 2, and an observation optical path P2 is divided from a photographing optical path P1 by the dichroic mirror 25. After infrared reflection light from the fundus Ef reflected by the dichroic mirror 25 passes through a relay lens 30, it is further reflected by a dichroic mirror 31 having a property of reflecting infrared light and transmitting visible light, so as to enter a CCD camera 32 for observation having a sensitivity to the infrared range. Then, an image of the fundus Ef is formed on an image pickup surface of the camera 32.

Incidentally, the lens 23, which is movable along the optical axis of the optical path P0 shared by the photographing optical system 2 and the observation optical system 3, provides a way for correction (adjustment) of a refractive error to be consistent with a refractive power of the eye E. The lens 23 is fixedly disposed on a rack 42, and the rack 42 is engaged with a pinion 41 fixedly attached to a rotation shaft of a stepping motor 40. The lens 23 moves on the optical axis in conjunction with the rack 42 and the pinion 41 by rotation of the motor 40, and it may bring the image of the fundus Ef into focus on the image pickup surfaces of the cameras 27 and 32.

Focus Index Projection Optical System

The focus index projection optical system 45 has an index plate 47, an LED 46 for emitting infrared light, and a half mirror 48, wherein the index plate 47 and the LED 46 are movable together with the lens 23. After passing through the index plate 47, the infrared light for an index projection is reflected by the mirror 21 to form an image on a conjugate plane (not illustrated) with the fundus Ef once, and then it is projected onto the fundus Ef via the lens 20. As an image of the focus index is projected onto the fundus Ef by infrared light, its infrared reflection light is reflected by the dichroic mirrors 25 and 31 and is picked up along with the image of the fundus Ef by the camera 32.

Fixation Target Projection Optical System

The fixation target projection optical system 35 is disposed on the observation optical path P2 side divided from the photographing optical path P1 by the dichroic mirror 25. The dichroic mirror 31 further divides the observation optical path P2 into optical paths P3 and P4, and a fixation light source 36 emitting visible light is provided (disposed) on the optical path P4 divided from the optical path P3 on which the camera 32 is provided (disposed). The fixation light source 36, disposed at an end of an adjustment knob 37, is arranged to be movable within an approximately conjugate plane with the fundus Ef and the image pickup surface of the camera 32. The fixation light source 36 is moved within the plane vertical to the projection optical axis as an examiner operates the adjustment knob 37. Accordingly, the position of the fixation target presented to the eye E can be changed, and the fundus Ef can be guided to a desired position for photographing.

The visible light emitted from the fixation light source 36 is transmitted through the dichroic mirror 31 and enters the dichroic mirror 25 via the lens 30. Although approximately only 20% to 10% of the visible light (the fixation target) having entered the dichroic mirror 25 is reflected, the visible light proceeds along the shared optical path P0 to be visible to the eye E and to induce eye fixation by the eye E. Besides, instead of the dichroic mirror 31, a half mirror may be used.

Figure 2:
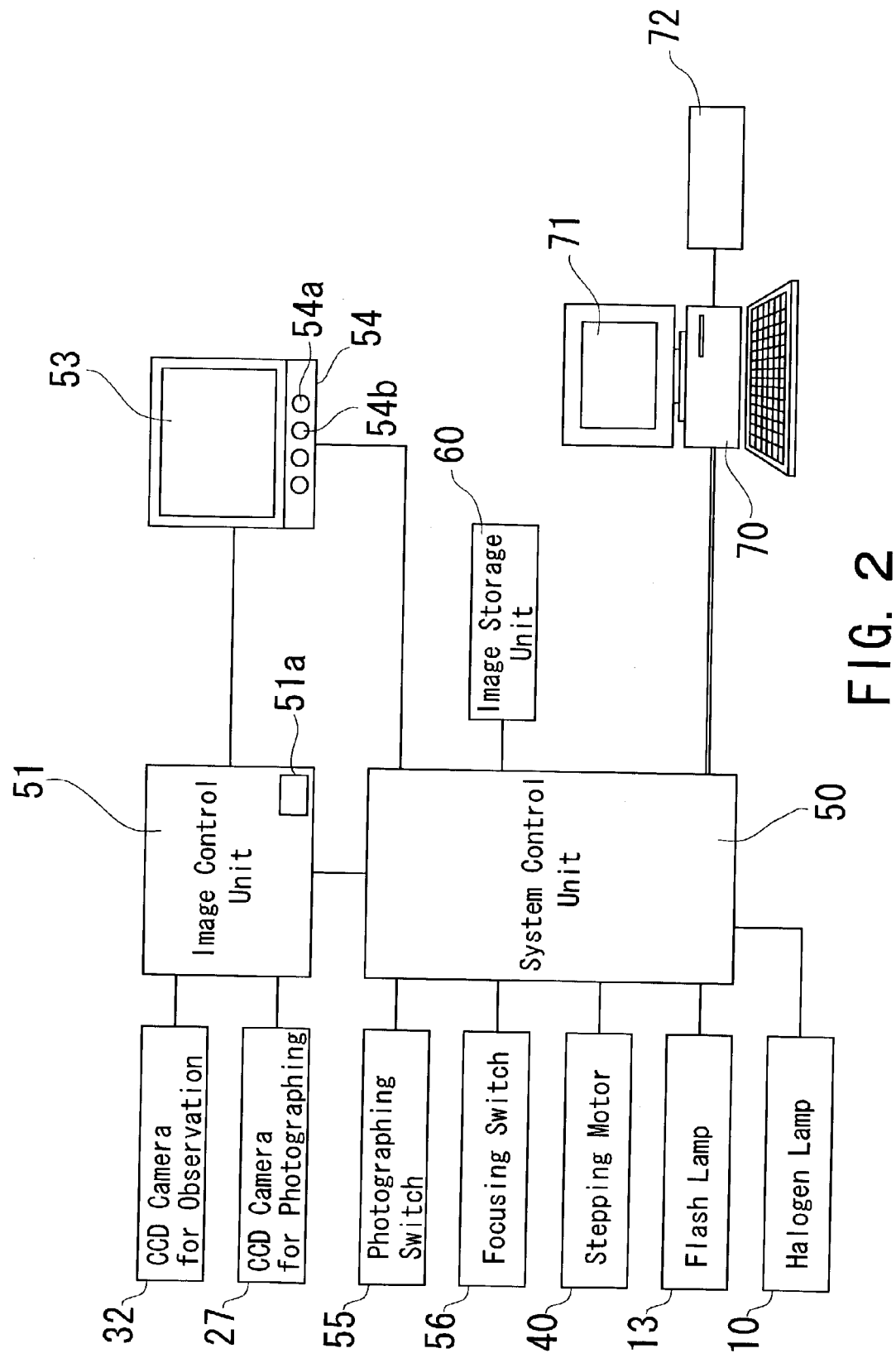
FIG. 2 is a view showing a schematic configuration of primary units of a controlling system of the fundus camera.

Next, as to the fundus camera having the above-mentioned structure, a description of functions of primary units in a control system of the fundus camera will be given referring to FIG. 2 showing a schematic configuration of the system.

First, as preparation for photographing the eye E, an alignment between the eye E and the optical system is performed. The optical system stored in a casing is put on a movable base, and it makes a relative movement to a fixed base by a sliding mechanism, which is not indicated in the figure. After the head of an examinee is fixed on a chin rest disposed on the fixed base, the eye E is illuminated by infrared illumination light by turning on the lamp 10. Infrared reflection light from the fundus Ef is reflected by the dichroic mirror 25, and an image of the eye E is picked up by the camera 32. Picture signals from the camera 32 are inputted to an image control unit 51. To the image control unit 51, a color liquid crystal display (LCD) 53 is connected, and the image of the eye E (an observation image) is displayed thereon. While observing the image of the eye E (a monochrome moving image (live image) at this point) shown on the LCD 53, the examiner observes an alignment reflex formed by an alignment optical system not shown in the figure in order to perform alignment for adjustment of the working distance between the eye E and the optical system and for adjustment of the optical axes.

After completing the alignment, the examiner moves the lens 23 by operating a focusing switch 56 so that the image pickup surfaces of the cameras 27 and 32 are placed at conjugate positions with the fundus Ef. A system control unit 50 rotates the motor 40 in accordance with an operational signal from the switch 56 and moves the lens 23 along the optical axis. This operation is done to correct the gap in a focus position derived from a refractive error of the eye E, to adjust the focus on the fundus Ef, and to form a clear image of the fundus Ef. As mentioned before, as the visible light emitted from the fixation light source 36 is reflected by the dichroic mirror 25 and projected onto the fundus Ef, the visible light can be clearly recognized due to correction of a refractive error of the eye E, and then the examinee can fixate his/her eye to the light emitted from the fixation light source 36.

The image of the focus index (an image on the index plate 47) picked up by the camera 32 along with the image of the fundus Ef by the camera 32 is utilized for adjusting the focus by moving the lens 23. While observing the fundus image and the image of the focus index picked up by the camera 32 and displayed on the LCD 53, the examiner operates the switch 56 to adjust the focus of the image of the focus index. By doing this operation, it is possible to correct the gap in a focus position derived from the refractive error of the eye E (a varied amount of a refractive power diopter of the eye E).

After completing adjustment of the focus to observe an image of the fundus Ef to be photographed, the examiner generates a trigger signal by pressing a photographing switch 55. In response to input of the trigger signal, a control unit 50 causes firing (lighting) to the lamp 13 in order to illuminate the fundus Ef with visible illumination light. Visible reflection light from the fundus Ef enters the camera 27 as it proceeds along the optical path mentioned above. Picture signals from the camera 27 are inputted to the image control unit 51, and a color still picture of the fundus image is stored in an image memory 51a included in the image control unit 51 in synchronism with the firing (lighting) of the lamp 13.

A size of the fundus image picked up by the camera 27 varies according to a travel (moving) position of the lens 23. The control unit 50 detects positional information of the lens 23 as photographed based on the number of rotarypulses of the motor 40, whereby obtaining variation information of photographing magnification (the varied amount of the diopter), in other words, obtaining the size of the fundus image corresponding to the positional information. The size of the fundus image may be obtained by preprogramming a correlation between the position of the lens 23 and the magnification variation calculated based on the position from the viewpoint of optical design. Besides, an encoder or the like may detect the positional information of the lens 23.

The image control unit 51 graphically generates a display frame figure having, for example, a circular opening (reference numeral 80 in FIG. 3) for determining a visual field range, and synthesizes the display frame figure with the fundus image stored in the image memory 51a to be displayed on the LCD 53. At this time, the image control unit 51 changes the opening size of the display frame figure which is displayed graphically, in accordance with data about the size of the fundus image obtained by the control unit 50, in order to fix a field angle. In the meantime, while it is provided herein that the observation image and the photographed image are displayed on the same LCD 53, they may be respectively displayed on their exclusive displays.

Figure 3A:
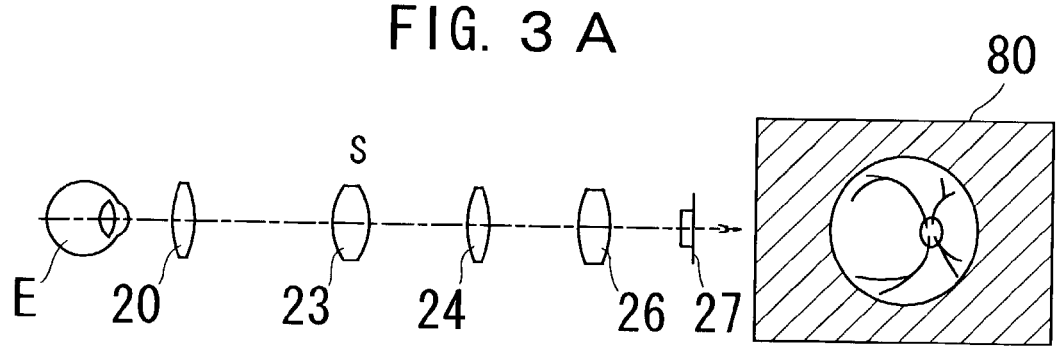
FIGS. 3A to 3C are views indicating a relationship between a position of a focusing lens and a fundus image displayed on a display.
Figure 3B:
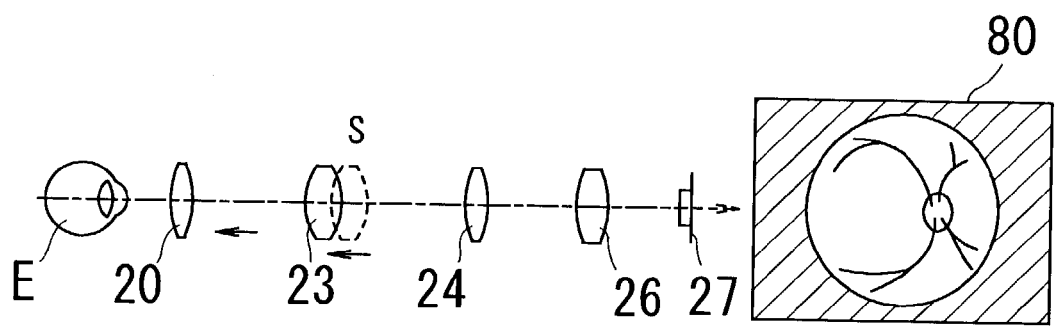
Figure 3C:
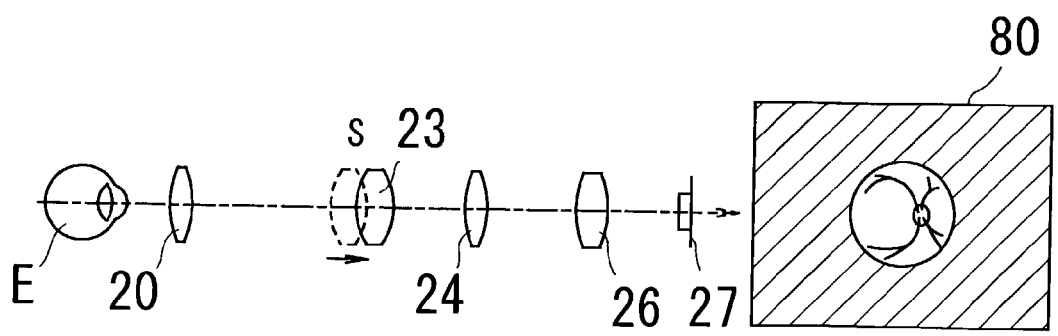
Figure 4A:
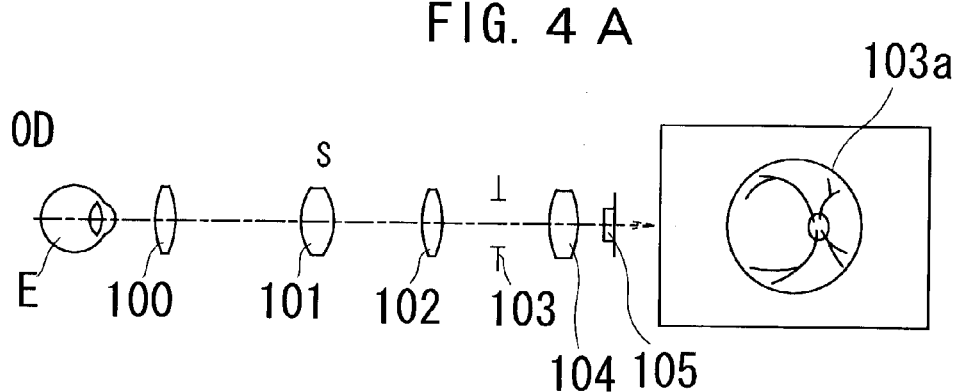
FIGS. 4A to 4C are views indicating a state of the fundus image which is conventionally obtained when a focusing lens is moved.
Figure 4B:
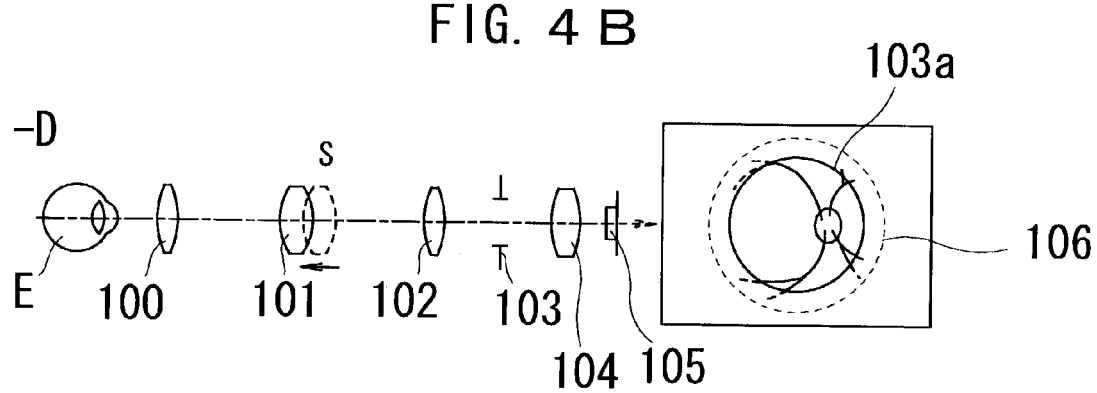
Figure 4C:
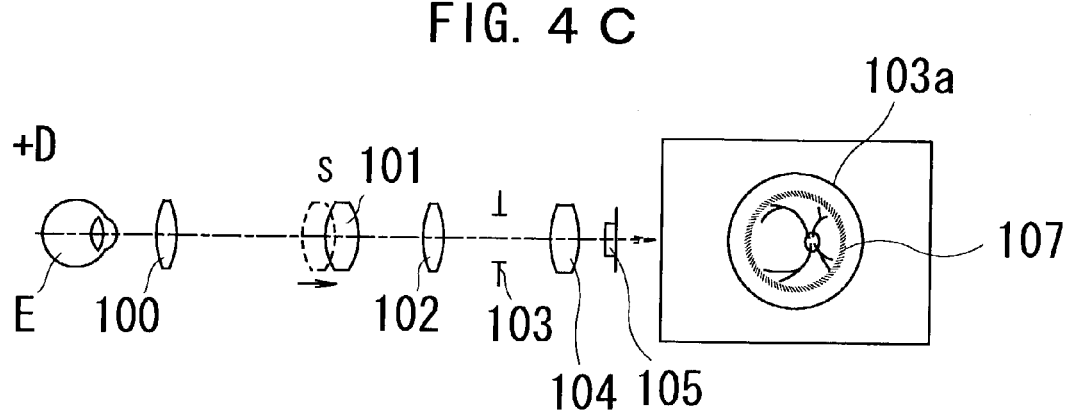

FIGS. 3A to 3C are views indicating a relationship between the position of the focusing lens 23 and the fundus image displayed on the LCD 53. FIG. 3A shows a case where the focus adjustment is made with the eye E under the conditions of emmetropia (0D). FIG. 3B shows a case where the focus adjustment is made with the eye E under the conditions of myopia (−D), and the size of the fundus image is expanded compared with that in FIG. 3A. FIG. 3C shows a case where the focus adjustment is made with the eye E under the conditions of hypermetropia (+D), and the size of the fundus image is shrunk compared with that in FIG. 3A. On the LCD 53, the display frame FIG. 80 having a black background is graphically displayed, and the size of its opening is also changed in accordance with the size of the fundus image by the movement of the lens 23. The opening of the display frame FIG. 80 is formed to have a size where a blurred portion at the periphery of an image circle would be cut from the fundus image being picked up. Such display allows the examiner to obtain the fundus image having the fixed field angle, even if the refractive power of the eye to be examined is varied (regardless of a condition of the fundus).

In the meantime, as to the graphical display of the display frame FIG. 80, the one is also included where the fundus image data being picked up would be trimmed in accordance with the aforementioned size of the fundus image, and processed synthetically to a background in black or the like. The shape of the opening of the display frame FIG. 80 is not limited to a circular shape, and it may be a rectangular shape, or an oval shape being horizontally oriented. Further, the opening may be provided with a cut away portion at the upper right thereof to be asymmetrical in right-and-left and up-and-down so that the right-and-left and up-and-down of the displayed image (the photographed image) may be identified when it is printed out.

The control unit 50 is connected with an image storage unit 60 capable of storing a large amount of image data such as an MO (a magneto-optical disk) or a memory card. By pressing an image storing switch 54a disposed on an input unit 54, the fundus image data stored in the image memory 51a is stored in the image storing unit 60. At this time, the opening size data of the display frame FIG. 80 (trimming size data) used for the display is also attached to (stored in association with) the fundus image data.

The image data stored in the image storing unit 60 and the size data attached to the image data may be output and sent to an external computer 70 connected by a communication cable by pressing a data sending switch 54b. When the memory card is used as the image storing unit 60, the data stored in the memory card may be sent in a manner that the external computer 70 reads them. Further, in the case of displaying the fundus image on a display 71 of the external computer 70, the attached opening size data of the display frame FIG. 80 is used to display the fundus image having the same display frame FIG. 80 as that of the LCD 53. In addition, at the time of printing out by a printer 72, the fundus image having the display frame FIG. 80 is printed out. Needless to say, it is possible to display and print out a raw image as photographed.

Besides, where the raw image as photographed is not particularly needed, the fundus image to which the display frame FIG. 80 is synthetically processed (obtained by the image control unit 51 as a result of image processing) may be stored in the image storing unit 60.

Owing to the display frame FIG. 80 as described above, the fundus image keeping a fixed field angle may be obtained regardless of visibility of the eye to be examined. Therefore, not only for photographing a posterior pole of the fundus but also for associating with peripheral photographing, it is advantageous because there is no influence of the conventional display frame being fixedly arranged. For example, it is easy to create a panoramic image in which fundus images are connected, and the connection may be attained favorably.

In the previous description, the display frame FIG. 80 is displayed for the photographed image (the color still image) by the camera 27, and it is convenient if the display frame FIG. 80 is displayed also for the observation image (the monochrome moving image) by the camera 32. The image control unit 51 graphically displays the display frame FIG. 80 having the opening for the live image (the moving fundus image) being displayed on the LCD 53, based on the size of the fundus image obtained by the positional information of the lens 23 in the same manner as mentioned before. In such an event, the display frame FIG. 80 is synthetically displayed with the observation image. This process enables the observation image to avoid inconsistency of field angle with the photographed image.

As described above, according to the present invention, it is possible to obtain the fundus image while keeping the field angle fixed even if the eye to be examined has varied refractive power, by properly grasping the magnification (the size) of the fundus image to be varied in accordance with the movement of the focusing lens, without complicating a unit configuration.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera for photographing a fundus of an eye to be examined comprising:
   a photographing optical system having a photographing optical axis, a focusing lens arranged movable along the photographing optical axis in an optical-axis direction, and a first image pickup element which picks up an image of the fundus illuminated with illumination light for photographing via the focusing lens;
   a moving unit which moves the focusing lens;
   a detecting unit which detects a position of the focusing lens;
   a display; and
   a display control unit which synthesizes the fundus image picked up by the first image pickup element within an opening of a display frame figure, a size of the opening being determined based on a result of detection obtained by the detecting unit, to display as an image keeping a fixed field angle regardless of visibility of the eye, and displays the fundus image on the display.

2. The fundus camera according to claim 1, further comprising an observation optical system having a second image pickup element which picks up an image of the fundus illuminated with illumination light for observation via the focusing lens,
   wherein the display control unit synthesizes the fundus image picked up by the second image pickup element within the opening of the display frame figure, the size of the opening being determined based on the result of detection obtained by the detecting unit, to display as an image keeping the fixed field angle regardless of the visibility of the eye, and displays the fundus image on the display.

3. The fundus camera according to claim 1, further comprising a memory which associates and stores data on the fundus image and data on the opening size.

4. The fundus camera according to claim 1, further comprising an output unit which associates and outputs data on the fundus image and data on the opening size.

5. A fundus camera for photographing a fundus of an eye to be examined comprising:
   a photographing optical system having a photographing optical axis, a focusing lens arranged movable along the photographing optical axis in an optical-axis direction, and a first image pickup element which picks up an image of the fundus illuminated with illumination light for photographing via the focusing lens;
   a moving unit which moves the focusing lens;
   a detecting unit which detects a position of the focusing lens;
   a display; and
   a display control unit which trims the fundus image picked up by the first image pickup element into a size based on a result of detection obtained by the detecting unit, to display as an image keeping a fixed field angle regardless of visibility of the eye, and displays the fundus image on the display.

6. The fundus camera according to claim 5, further comprising an observation optical system having a second image pickup element which picks up an image of the fundus illuminated with illumination light for observation via the focusing lens,
   wherein the display control unit trims the fundus image picked up by the second image pickup element into the size based on the result of detection obtained by the detecting unit, to display as an image keeping the fixed field angle regardless of the visibility of the eye, and displays the fundus image on the display.

7. The fundus camera according to claim 5, further comprising a memory which associates and stores data on the fundus image and data on the trimming size.

8. The fundus camera according to claim 5, further comprising an output unit which associates and outputs data on the fundus image and data on the trimming size.

* * * * *